United States Patent
Cohen et al.

(10) Patent No.: US 12,318,623 B2
(45) Date of Patent: Jun. 3, 2025

(54) DEVICE AND METHOD FOR REAL-TIME CLOSED-LOOP BRAIN STIMULATION

(71) Applicant: BRAINSWAY LTD., Har Hotzvim (IL)

(72) Inventors: Roie Cohen, Jerusalem (IL); Samuel Zibman, Neve Daniel (IL); Abraham Zangen, Jerusalem (IL); Yiftach Roth, Rechelim (IL)

(73) Assignee: BRAINSWAY LTD., Har Hotzvim (IL)

( * ) Notice: Subject to any disclaimer, the term of this patent is extended or adjusted under 35 U.S.C. 154(b) by 1008 days.

(21) Appl. No.: 17/051,221

(22) PCT Filed: Apr. 30, 2019

(86) PCT No.: PCT/IL2019/050482
§ 371 (c)(1),
(2) Date: Oct. 28, 2020

(87) PCT Pub. No.: WO2019/211845
PCT Pub. Date: Nov. 7, 2019

(65) Prior Publication Data
US 2021/0361967 A1    Nov. 25, 2021

Related U.S. Application Data

(60) Provisional application No. 62/665,066, filed on May 1, 2018.

(51) Int. Cl.
*A61B 5/377*     (2021.01)
*A61N 2/00*      (2006.01)
(Continued)

(52) U.S. Cl.
CPC .............. *A61N 2/006* (2013.01); *A61B 5/377* (2021.01); *A61N 2/02* (2013.01); *A61B 5/055* (2013.01);
(Continued)

(58) Field of Classification Search
CPC .... A61B 5/377; A61B 5/4836; A61N 1/0456; A61N 1/0529–0539; A61N 1/36025
See application file for complete search history.

(56) References Cited

U.S. PATENT DOCUMENTS

| 6,256,531 B1 | 7/2001 | Ilmoniemi et al. |
| 2004/0034886 A1 | 2/2004 | Cahoon et al. |

(Continued)

FOREIGN PATENT DOCUMENTS

| CN | 104394931 A | 3/2015 |
| JP | 2008516696 A | 5/2008 |

(Continued)

OTHER PUBLICATIONS

Gharabaghi, et al., "Coupling brain-machine interfaces with cortical stimulation for brain-state dependent stimulation: enhancing motor cortex excitability for neurorehabilitation", Frontiers in Human Neuroscience, vol. 8, Article 122, Mar. 5, 2014, pp. 1-7.

(Continued)

*Primary Examiner* — Thaddeus B Cox
(74) *Attorney, Agent, or Firm* — Dorsey & Whitney LLP (57) ABSTRACT

Brain stimulation techniques are disclosed, utilizing a brain state monitoring and stimulating component having at least one processor and memory, and a digital signal processing unit configured and operable to predict at least one brain state about to occur in a brain of a treated subject based on data or signals indicative of at least one brain state of the treated subject. The digital signal processing unit can be configured to generate based on the predicted at least one brain state stimulation data for adjusting, regulating or triggering, brain stimulation signals applied to the brain of the treated subject. The at least one processor, memory, and digital signal processing unit are embedded in some embodiments in a single hardware device.

33 Claims, 5 Drawing Sheets

(51) Int. Cl.
   *A61N 2/02*   (2006.01)
   *A61B 5/00*   (2006.01)
   *A61B 5/055*   (2006.01)

(52) U.S. Cl.
   CPC .............. *A61B 5/4836* (2013.01); *A61B 5/72* (2013.01); *A61B 2560/02* (2013.01)

(56) References Cited

U.S. PATENT DOCUMENTS

| | | | |
|---|---|---|---|
| 2005/0107655 A1 | 5/2005 | Holzner | |
| 2013/0066392 A1 | 3/2013 | Simon et al. | |
| 2014/0303424 A1 | 10/2014 | Glass | |
| 2016/0077547 A1* | 3/2016 | Aimone | A61B 5/378 345/8 |
| 2016/0188827 A1* | 6/2016 | Warner | A61B 5/40 702/19 |
| 2016/0220836 A1 | 8/2016 | Parks | |
| 2017/0027812 A1* | 2/2017 | Hyde | G16H 10/20 |
| 2017/0113056 A1* | 4/2017 | Stocco | A61N 1/0476 |
| 2018/0133507 A1* | 5/2018 | Malchano | H05B 47/105 |
| 2019/0134395 A1* | 5/2019 | Fitzgerald | A61N 1/36025 |
| 2020/0237296 A1* | 7/2020 | Schiff | A61B 5/4821 |

FOREIGN PATENT DOCUMENTS

| | | |
|---|---|---|
| WO | 2006044793 A2 | 4/2006 |
| WO | 2014140432 A1 | 9/2014 |
| WO | 2017189757 A1 | 11/2017 |

OTHER PUBLICATIONS

Zrenner, et al., "Real-time EEG-delned excitability states determine ef!cacy of TMS-induced plasticity in human motor cortex", ScienceDirect, Brain Stimulation, vol. 11, 2018, pp. 374-389.

* cited by examiner

DEVICE AND METHOD FOR REAL-TIME CLOSED-LOOP BRAIN STIMULATION

TECHNOLOGICAL FIELD

The present invention is generally in the field of brain stimulation.

BACKGROUND

Transcranial magnetic stimulation (TMS) therapy can be used for treating various mental/psychological, neurological (CNS) and/or physiological disorders. TMS implementations are based on Faraday's law of electromagnetic induction, by which brief magnetic pulses directed to specific brain regions of a subject induce targeted neuronal depolarization in the brain tissue. When TMS is carried out in a repetitive fashion, which is known as rTMS, or in other pulse patterns, neuroplastic long-term-potentiation-like or depression-like effects can be achieved. The availability of this technology is dramatically changing the practice of psychiatry and neurology, as well as the perception of mental illness.

TMS systems usually follow an open-loop paradigm, wherein pre-programmed stimulation parameters are used throughout an entire treatment session, regardless of chemical/electrical states of the subject's brain. Closed-loop TMS systems rely on sensor feedback to monitor the states of the subject's brain in order to adjust stimulation parameters accordingly. Such closed-loop systems can automatically adjust the duration, timing, intensity and stimulation pattern, of the applied stimulation pulses to achieve the desired therapeutic results. Monitoring and analyzing brain activity requires precise and accurate measurements of features, such as, instantaneous phase, amplitude, and spectrum for accurately determining stimuli parameters. Thus, closed-loop brain stimulation applications require powerful and fast processing resources, including high temporal resolution acquisition system with non-buffered data transfer together with a rapid signal analysis capability, which currently render real-time closed-loop brain stimulation applications impractical or too expensive.

A. Gharabaghi et al., ("*Coupling brain-machine interfaces with cortical stimulation for brain-state dependent stimulation: enhancing motor cortex excitability for neurorehabilitation*", Frontiers in Human Neuroscience, 2014), reports a study of brain state-dependent stimulation (BSDS) combined with haptic feedback provided by a robotic hand orthosis, in which TMS of the motor cortex and haptic feedback to the hand were controlled by sensorimotor desynchronization during motor-imagery and applied within a brain-machine interface (BMI) environment. The BSDS is reported to significantly increase the excitability of the stimulated motor cortex in both healthy and post-stroke subjects, an effect not observed in non-BSDS protocols. This feasibility study suggests that closing the loop between the intrinsic brain state, cortical stimulation and haptic feedback provides a novel neurorehabilitation strategy for stroke patient lacking residual hand function, a proposal that warrants further investigation in a larger cohort of stroke patients.

C. Zrenner et al., ("*Real-time EEG-defined excitability states determine efficacy of TMS-induced plasticity in human motor cortex*", Brain Stimulation 2018, 11(2):374-389) describe state-dependent electroencephalography-triggered transcranial magnetic stimulation (EEG-TMS) applied to target the EEG negative vs. positive peak of the sensorimotor μ-rhythm in healthy subjects using a millisecond resolution real-time digital signal processing system. In this study corticospinal excitability was indexed by motor evoked potential amplitude in a hand muscle.

US Patent publication No. 2016/0220836 describes device and method for phase-locking brain stimulation to electroencephalographic rhythms for improving the accuracy, specificity, and effectiveness of non-invasive brain stimulation devices by timing pulses of brain stimulation to occur in synchrony with naturally occurring brain rhythms measured at the scalp of a patient in order to treat an assortment of neurological and psychiatric conditions. The device and method intend to improve non-invasive brain stimulation techniques by time-locking the onset of brain stimulation to the phase of naturally-occurring rhythmic oscillations of brain activity that can be recorded with electroencephalography (EEG). The device and method perform real-time signal analysis of a specified EEG rhythm, extract frequency-domain phase information to estimate the next occurrence of a desired EEG rhythm phase, and trigger a brain stimulation pulse so as to align precisely with this predicted EEG phase.

General Description

Heretofore brain state dependent non-invasive brain stimulation (BSDS) has been mostly employed for two main applications: (i) for stroke recovery, in which TMS pulses are triggered by beta band event related desynchronization during a motor imagery task (see, e.g., Gharabaghi et al., 2014) and for phase locking in the alpha band of repetitive TMS protocols (see, e.g., Zrenner et al., 2018). These applications however rely on predictive models that predict the current brain state based on the immediately prior brain rhythms. This operation scheme is required in such applications due to processing and computational delays which prevent determining the true instantaneous brain state of the treated subject in real time. In addition, the brain stimulation techniques of the prior art publications rely on communication between the brain state analysis and acquisition/recording units via a relaying component which has a significant impact on the timing restriction.

Prior art systems are not only slow but are also capable of only triggering a stimulating TMS pulse without changing its characteristics and/or pattern in real time i.e., they are not capable of adjusting the stimulating signals while they are being applied to the treated subject. This limitation is partly due to the limited processing and data communication speeds of the state of the art brain stimulation systems, and also because the applicator devices being thereby used are not designed to allow real time adjustments to the applied signals, but rather to apply a stimulating signal having a fixed shape and time pattern.

The present application provides a fast real-time and accurate closed-loop brain stimulation system configured and operable to continuously, periodically or intermittently, receive/read brain state signals/data indicative of at least one brain state measured, or being induced, in a treated subject, analyze the brain state signals/data to extract various features therefrom, predict based on the brain state signals/data and/or the extracted features at least one brain state about to occur in the brain of the treated subject, and generate brain stimulation parameters and/or timing data for use by a brain stimulation applicator. The generation of the brain stimulation parameters and/or timing data to be used in the brain stimulation applicator can be based entirely, or at least partially, on the predicted at least one brain state. Optionally, generation of the brain stimulation parameters and/or timing data to be used in the brain stimulation applicator is based entirely, or at least partially, on the brain state signals/data and/or on the features extracted therefrom.

In possible applications the brain stimulation system generates the brain stimulation parameters and/or timing data based entirely, or at least partially, on at least one brain state that occurred in the past in the brain of the treated subject, without predicting future brain states that are about to occur. For example, the brain stimulation system can be configured to apply to a treated subject one or more brain stimulations (e.g., TMS pulse, train of TMS pulses, visual stimulation, auditory stimulation, or any combination thereof), read brain state signals/data indicative of at least one brain state measured in the treated subject responsive to the applied brain stimulation, and generate new brain stimulation parameters and/or timing data to be used in the brain stimulation applicator based at least partially on the measured brain state signals/data, and/or based on one or more other brain state signals/data previously measured in the treated subject responsive to one or more previously applied past brain stimulations.

The brain stimulation applicator is configured to receive the brain stimulation parameters and/or timing data, and based thereon generate and apply (e.g., by TMS coils and/or current stimulating electrodes) one or more stimulation signals in at least one region/area of the brain of the treated subject, and/or apply one or more sensory stimuli (e.g., by sound/voice generator/player, 2D/3D display/holographic device, and/or haptic/tactile stimulator transducers). The brain stimulation applicator is configured to receive new brain stimulation parameters and/or timing data from the system and adjust in real-time the stimulation signals thereby applied according to the newly received brain stimulation parameters and/or timing data, and thereby enable the brain stimulation system to adapt in real-time the stimulation signals being applied to the current brain state data/signals measured by the system.

The brain stimulation system is configured to repeatedly perform these steps for continuously stimulating at least one brain region/area of the treated subject for a determined period of time. Optionally, such continuous brain stimulation are carried out using either a brain state measurements algorithm, or according to predefined limits. In this way the stimulation signals applied by the brain stimulation applicator can be dynamically adjusted/synchronized to features of the received/read brain state signals/data measurements to obtain a biofeedback brain stimulation process. Accordingly, the brain stimulation signals generated by the brain stimulation applicator are modulated/regulated in some embodiments by at least one feature extracted from the brain state signals/data to dynamically adjust any of the following features: the frequency, amplitude, stimulation pattern, current polarity, exact location of the brain stimulation signals.

Prior art brain stimulation systems often uses transistor-transistor logic triggering which limits the output stimulation to a single stimulation pattern. The brain stimulation system of the present application provides fuller integration with the brain stimulation applicator (e.g., TMS and/or sensory stimulator), thereby allowing application of different stimulation patterns, and real-time adaptation of the applied stimulation signals, depending on different brain state signals/data (e.g., EEG signals) measured by the system, instead of applying one single output pattern whenever a preset target signal is identified.

In order to effect the desired stimulations in at least one brain region/area of the treated subject the data processing and analyzing, feature extraction, brain state prediction, and/or stimulating signals parameters/timing/shaping data generation steps should be carried out very quickly and accurately. These goals are achieved in the brain stimulation systems of the present application using one or more processors (central processing units—CPUs) configured and operable to operate a digital signal processing (DSP) unit by a real-time operating system (RTOS, e.g., Abassi, AMOS, NI Linux Real-Time), which are all implemented entirely by hardware (e.g., FPGA/GPU). The brain stimulation system applications disclosed herein are thus suitable for system on chip (SoC) implementation, which can contribute to improve performance and miniaturization of geometrical dimensions of the system.

To further improve the processing speed of the brain stimulation system the one or more processors and/or the DSP unit are configured to exchange data using a fast communication protocol (FCP). Additionally, or alternatively, the one or more processors and/or the DSP unit are configured for direct memory access (DMA), to allow the processing units of the system to read/write data from/in the memory (e.g., RAM, SDRAM, FLASH) of the system without requiring interruption in their continuous operations.

Another advantage of the present application is the ability of direct communication with the brain state measurement equipment (e.g., EEG unit/system, fMRI, cognitive task application) without using relaying intermediate components. Conventional brain stimulation systems typically utilize software modules (i.e., supplied by the manufacturer) of the measurement equipment to communicate the measured brain state data e.g., by streaming over the network or some other API software tools. However, such software modules typically add another layer of complexity and uncertainty, which increases the delay time of receiving the measured brain state data/signals by the brain stimulation system. The brain stimulation system disclosed herein are configured to communicate directly with the brain state measurement equipment, without intermediate software layers of communication, to thereby significantly diminish the acquisition time of the measured brain state data/signals by the system and improve the ability to control and shape the stimulation signals responsively applied to the treated subject by the system.

Hardware implementations of the brain stimulation systems disclosed herein substantially reduces the processing and computation time, as compared to conventional brain stimulation systems e.g., by tens of milliseconds, thereby allowing allocation of substantially more time and resources for the prediction of future brain states that are likely to occur, for real-time formation of suitable stimulation signals correspondingly, and for significantly improving the precision of the prediction models and the effectivity of the applied stimulation signals.

In some embodiments the brain state signals/data are received from electroencephalogram (EEG) electrodes and the brain stimulation system is configured to perform spectral analysis to identify dominant frequency bands in the brain state signals/data and perform time-frequency analysis. The system can then extract various features related to the frequency (e.g., frequency data, phase data, amplitude data), and/or time (amplitude, time delay, etc.) domain, and/or perform brain connectivity analysis of either the frequency or time domain features of the brain state signals/data, and perform the brain state prediction and the generation of the respective brain stimulation parameters and/or timing data accordingly.

Alternatively, or additionally, the brain stimulation system is configured and operable to use transcranial alternating current stimulation (tACS) signals/data, received from tACS device and/or electrodes used for inducing desired brain state(s) in at least one region/area of the brain of the treated subject. The tACS signals/data can be similarly processed by the brain stimulation system to predict one or more brain states that are about to occur in the brain of the treated subject, and for generating corresponding operational parameters and/or timing data for operating the brain stimulation applicator to apply respective stimuli to the subject accordingly.

The predictive power of any model degrades with time and therefore performance of the prediction model can be improved by shortening the brain stimulation system's delays. The fast and real-time implementations of the brain stimulation system disclosed herein allow expanding the utility of the system for treating subjects which heretofore been categorized as not suitable for closed-loop BSDS. For example, in Zrenner et a/42018) there is a limitation of the algorithms that were used for the phase locking that enable phase locking of alpha band brain waves only when the power in the alpha band is at least 25% of the total power of the measured signals. This limitation excluded 50% of potential subjects and precludes phase locking to other bands in all subjects. However, this limitation of the prior art systems can be overcome by the real-time data processing of the brain stimulation systems of the present application. This can also be addressed by the inclusion of additional algorithms, not applicable in the prior art solutions due to their limited data/signals acquisition and processing capabilities, such as but not limited to, back propagation (BP) feedback models.

In particular, a main problem of the low power brain wave signals is the accuracy of the filtering applied thereto (which is made worse due to the fact that brainwaves are not purely sinusoidal). Thus, BP feedback is used in some embodiments in order to enhance the brain stimulation system capability to reliably process and react to such low power brain state measurement signals situation, by using feedback from offline evaluation of the stimulation phase, and/or brain wave signals measured responsive to previously applied stimulation signals, to correct imprecisions in the online algorithm. This way, the BP feedback can be used to determine which of the measured brain state values is most accurately indicative of a time for applying, and/or adjusting, the stimulation signals by the applicator.

Brain stimulation systems disclosed herein generally comprise a brain state monitoring and stimulating component comprising at least one processor, memory, and digital signal processing unit, embedded in a single integrated circuit device (e.g., SoC) configured and operable to receive and process data/signals indicative of at least one brain state of a treated subject and generate based thereon stimulation data for adjusting, regulating or triggering, in real-time brain stimulation signals applied to the brain of the treated subject. The digital signal processing unit is configured in some embodiments to predict at least one brain state that is occurring, or about to occur, in the brain of the treated subject, and generate based on the predicted at least one brain state the stimulation data for adjusting, regulating or triggering, in real-time the brain stimulation signals applied to the brain of the treated subject. Optionally, but in some embodiments preferably, the at least one processor and/or digital signal processing unit are operated utilizing a real-time operating system embedded in the integrated circuit device.

A stimulation generator electrically connected/coupled to the integrated circuit device can be used to generate brain stimulations to be applied to the brain of the treated subject, based on the stimulation data generated by the digital signal processing unit of the integrated chip device. The stimulation generator can be electrically connected to the integrated chip device by conductors (e.g., using serial or parallel bus data communication protocols), and/or wirelessly coupled to the integrated circuit device for wireless data communication therewith (e.g., using WiFi, Zigbee, Bluetooth, or suchlike). The stimulation generator is configured in some embodiments to adjust in real-time at least one of a shape, timing, and/or frequency, of the generated brain stimulations, based on the stimulation data generated by the digital signal processing unit of the integrated chip device. This way, the brain stimulation system can quickly acquire and process the data/signals indicative of at least one brain state of a treated subject, generate and communicate corresponding stimulation data to the stimulation applicator, and instantly generate and adjust brain stimulation signals applied to the brain of the treated subject.

One inventive aspect of the subject matter disclosed herein relates to a brain stimulation system comprising a brain state monitoring and stimulating component having at least one processor and memory, and a digital signal processing unit configured and operable to predict at least one brain state about to occur in a brain of a treated subject based on data/signals (e.g., associated with EEG electrodes, and/or tACS electrodes, and/or fMRI, and/or cognitive tasks performed by the treated subject) indicative of at least one brain state of the treated subject. The digital signal processing unit is configured to generate, based on the predicted at least one brain state and/or the data/signals, stimulation data for adjusting, regulating or triggering, brain stimulation signals applied to the brain of the treated subject. Optionally, but in some embodiments preferably, the at least one processor, memory, and/or digital signal processing unit are embedded in a single hardware device (e.g., SoC). The at least one processor and/or digital signal processing unit are operated in some embodiments utilizing a real-time operating system.

Optionally, but in some embodiments preferably, the digital signal processing unit is configured and operable to repeatedly receive the data/signals indicative of a current brain state of the treated subject, predict at least one brain state about to occur in the subject based on the received data/signals, and generate the stimulation data/signals for application of a new stimulation cycle, to thereby provide a closed-loop brain stimulation mechanism capable of regulating the brain stimulation signals applied to the treated subject according to the generated stimulation data. Optionally, the regulating of the brain stimulation signals comprises modulating the brain stimulation signals by the generated stimulation data.

The at least one processor and the digital signal processing unit are configured in some embodiments to exchange data using a fast communication protocol. Alternatively, or additionally, the at least one processor and the digital signal processing unit are configured and operable to read and write data from/in the memory of the system by direct memory access scheme. To further improve performance in some embodiments the at least one processor, the digital signal processing unit, and memories thereof, are implemented in a single integrated circuit chip device, for example as a SoC (e.g., implementing the at least one processor in FPGA and the digital signal processing unit by a GPU on the same semiconductor substrate).

The digital signal processing unit comprises in some embodiments at least one digital filter module configured and operable to remove interferences from the data/signals indicative of the at least one brain state of the treated subject, and/or at least one analysis module configured and operable to process the received data/signals indicative of the at least one brain state of the treated subject and perform at least one of time-frequency analysis and spectral analysis thereof, and/or at least one feature extraction unit configured and operable to extract at least one feature indicative of at least one brain state of the treated subject from the received data/signals indicative of the at least one brain state of the treated subject, and/or spectral and/or time-frequency analysis data thereof, and/or at least one prediction module configured and operable to predict at least one brain state about to occur in the brain of the treated subject based on the received data/signals, and generate the stimulation data based on said predicted at least one brain state.

The digital signal processing unit comprises in some embodiments at least one artifacts rejection module configured and operable to automatically remove artifacts from the data or signals indicative of the at least one brain state of the treated subject. Optionally, the at least one artifacts rejection module is configured and operable to use an automated independent component analysis (ICA) real-time process for the removal of the artifacts.

The brain state monitoring and stimulating component comprises in some embodiments a communication module configured and operable to exchange data with at least one other device/system. The brain state monitoring and stimulating component can be accordingly configured and operable to communicate via the communication module treatment data associated with treatment protocols conducted by the system. The system comprises in some embodiments a database system for storing the treatment data communicated by the brain state monitoring and stimulating component via the communication module. The database system can be configured and operable to analyze the stored treatment data and generate statistical data associated therewith. Optionally, but in some embodiments preferably, the database system is configured and operable to utilize artificial intelligence tools in the analysis of the stored data.

The brain stimulation signals applied to the brain of the treated subject is associated in some embodiments with at least one of the following: audible stimulation, visual stimulation, TMS stimulation, tDCS stimulation, tACS stimulation, and/or tactile stimulation.

Another inventive aspect of the subject matter disclosed herein relates to a method for generating brain stimulations. The method comprising receiving data or signals indicative of at least one brain state of a treated subject, analyzing the received data or signals to determine at least one feature associated with the at least one brain state, predicting based on the determined at least one feature and/or the received data/signals at least one brain state about to occur (or occurred) in a brain of the treated subject, and generating stimulation data based on the predicted at least one brain state for application of stimulating signals to the brain of the treated subject.

Optionally, the method comprising at least one of filtering and processing the received data or signals indicative of the at least one brain state to respectively remove therefrom at least one of interferences and artifacts. The processing of the received data or signals indicative of the at least one brain state can comprise an independent component analysis process configured to automatically remove in real-time the artifacts from the received data or signals.

The method comprises in some embodiments continuously, periodically or intermittently, repeating through at least one treatment session the prediction of the at least one brain state and the generation of the stimulation data, for newly received data or signals indicative of at least one brain state of the treated subject. Optionally, but in some embodiments preferably, the generated stimulation data is configured for regulating/modulating the stimulating signals in accordance with variations in the at least one feature determined from the received data or signals. In some possible embodiments the generated stimulation data is associated with at least one of frequency, amplitude, stimulation pattern, current polarity, and/or exact location of the brain stimulation signals. This way, the generated stimulation can be used to adjust in real time the stimulation signals applied to the treated subject based on the data or signals indicative of the at least one brain state newly received in the system during its operation.

The method comprises in some embodiments storing treatment data indicative of the received data or signals and the generated treatment data in a database, analyzing the treatment data accumulated in the database, and generating analysis data indicative thereof. The analyzing of the treatment data comprises in some embodiments at least one of statistical analysis, machine learning, deep learning, or any combination thereof.

Functional magnetic resonance imaging (fMRI) is used in some embodiments to monitor brain activity of the treated subject. Data signal from the fMRI system can be used for determining brain states of a treated subject by the brain stimulation schemes described herein, in addition to, or instead of, the EEG and/or tACS data or signals.

The stimulation data can be generated based on brains states previously induced in the brain of the treated subject by the stimulating signals. Optionally, the stimulating signals comprise at least one of audio signals, visual signals, TMS signals, tDCS signals, or tACS signals. For example, and without being limiting, the method can be used to induce some activation in the brain of the treated subject by application of the brain stimulations, process the brain state data acquired thereafter to determine at least one reaction occurred in response to the applied brain stimulations, and generate new stimulation data accordingly for inducing a desired brain state. A response observed in the processed brain state data can be predictive of at least one future brain state of the brain of treated subject, and/or indicative of a current brain state, which can be used in the prediction process. For example, the prediction process can be implemented by pattern matching process configured to compare a pattern identified in the acquired brain state data to a known response, and accordingly determine the likelihood of a future brain state to responsively occur in the brain of the treated subject.

Another inventive aspect of the present application relates to an integrated circuit (IC) system comprising at least one processor, at least one memory, and at least one digital signal processing unit, configured and operable to receive and process brain state data or signals indicative of at least one brain state of a treated subject and generate based thereon stimulation data for adjusting, regulating or triggering, in real-time brain stimulation signals applied to the brain of the treated subject. The integrated circuit comprises in some embodiments a prediction module embedded therein and configured and operable to predict at least one brain state that is occurring, or about to occur, in the brain of the treated subject, based on the brain state data or signals, and generate based on the predicted at least one brain state the stimulation data. In addition, a real-time operating system can be embedded in the integrated circuit system for operating at least one processor and digital signal processing unit thereof.

The IC system comprises in some embodiments at least one digital filtering module embedded therein and configured and operable to remove interferences from the brain state data or signals. At least one artifacts rejection module can be also embedded in the IC system to apply an automated independent component analysis process for the removal of artifacts from the brain state data. Optionally, at least one analysis module embedded in the IC system is used to process the brain state data or signals and perform at least one of time-frequency analysis and spectral analysis thereof. At least one feature extraction module is also embedded in the IC system of some embodiments to extract at least one feature indicative of at least one brain state of the treated subject from the brain state data or signals.

Optionally, and in some embodiments preferably, a communication interface module is also embedded in the IC system for communicating data over at least one of wireless data communication and bus conductors data communication channels. Optionally, at least one processor or digital signal processing unit of the integrated circuit system is implemented in FPGA or as a GPU.

This way, a brain stimulation system can be implemented using the IC system and a stimulation generator electrically connected or coupled to the IC system and configured to receive the stimulation data from the at least one digital signal processing unit and based thereon generate, or adjust, in real-time brain stimulations to be applied to the brain of the treated subject.

BRIEF DESCRIPTION OF THE DRAWINGS

In order to understand the invention and to see how it may be carried out in practice, embodiments will now be described, by way of non-limiting example only, with reference to the accompanying drawings. Features shown in the drawings are meant to be illustrative of only some embodiments of the invention, unless otherwise implicitly indicated. In the drawings like reference numerals are used to indicate corresponding parts, and in which.

DETAILED DESCRIPTION OF EMBODIMENTS

This application discloses closed loop brain stimulation techniques and implementations configured to trigger and/or modulate/regulate brain stimuli according to real time brain state(s) determined based on EEG signals, and/or brain state frequency and phase rhythms obtained by transcranial alternating current stimulation (tACS), and/or a task dependent brain state achieved by input of external triggers (e.g., TMS pulses that induce a certain brain state, and/or sensory stimuli, such as but not limited to, auditory and/or visual, and/or haptic/tactile, stimulation), all of which generally referred to herein as brain state signals/data. Such real time implementations are difficult to achieve due to the amounts of data processing required to analyze the brain state signals/data involving filtering and cleaning the raw signal, determining source localization, spectrum analysis, phase locking, statistical computation and/or predictive model estimation, and the high data processing rates of performing these operations. Therefore, the design of real-time closed-loop brain stimulation solutions requires special and careful consideration for optimizing system performance and accuracy.

In some possible embodiments various data processing modules of real-time closed-loop brain stimulation systems are implemented in hardware (e.g., FPGA/GPU) configured for direct memory access (DMA), or any other suitable fast communication protocol (FCP), such as but not limited to, serial peripheral interface (SPI), two-wire interface (TWI), universal synchronous and asynchronous receiver-transmitter (USART), using one or more processing units that operates the hardware data processing modules using a real-time operating system (RTOS), to thereby substantially improve performance/speed of the system. The data processing hardware modules may comprise a preprocessing module, configured for referencing, source localization and signal filtering, a time-frequency analysis module, and a brain state prediction module. The brain state prediction module can be configured to use various features extracted from the brain state signals/data, such as but not limited to signal power spectrum, and/or signal amplitude, and/or signal timing, and/or brain connectivity measures such as phase locking value, to determine at least one parameter of the stimulation signals applied by the system, and generate triggering signals based thereon. Autoregressive forward prediction model can be used to update the prediction model over time based on peak frequencies identified by the system in the brain state signals/data.

A user interface unit is used in some embodiments to set various operational parameters (power threshold, target frequencies/phase, analysis type/time window, prediction model, processing steps) and/or conditions/states (target electrodes, stimuli patterns). This way specific stimuli triggering process, employing determined stimulation patterns, can be tailored for a specific subject for treating certain neurological/psychiatric conditions.

A subject interface unit is used in some embodiments to interact with the treated subject for inducing desired brain states in the treated subject. The subject interface unit can be configured to present to the user audio or visual, or audio-visual, content, and/or apply haptic stimuli, configured to induce the desired brain state, and/or to stimulate the brain using tACS electrodes to induce the desired brain state. Alternatively, or additionally, the subject interface unit can be configured to present to the treated subject specially designed tasks (cognitive tasks), and optionally receive from the treated subject corresponding inputs/feedbacks, usable by the system for inducing dependent brain state e.g., achieved by input of external triggers.

One or more specific embodiments of the present application will be described below with reference to the drawings, which are to be considered in all aspects as illustrative only and not restrictive in any manner. In an effort to provide a concise description of these embodiments, not all features of an actual implementation are described in the specification. Emphasis instead being placed upon clearly illustrating the principles of the invention such that persons skilled in the art will be able to make and use brain stimulation applications, once they understand the principles of the subject matter disclosed herein.

The embodiments described hereinbelow may be implemented in other specific forms without departing from the essential characteristics described herein. The embodiments illustrated schematically and diagrammatically in the figures are provided as example implementations that demonstrate a number of features, processes, and principles used to provide real-time closed-loop brain stimulation, but they are also useful for other applications and can be made in different variations. Therefore, this description will proceed with reference to the shown examples, but with the understanding that the invention recited in the claims below can also be implemented in myriad other ways, once the principles are understood from the descriptions, explanations, and drawings provided herein. All such variations, as well as any other modifications apparent to one of ordinary skill in the art and useful in brain stimulation applications may be suitably employed, and are intended to fall within the scope of this disclosure.

Figure 1A:
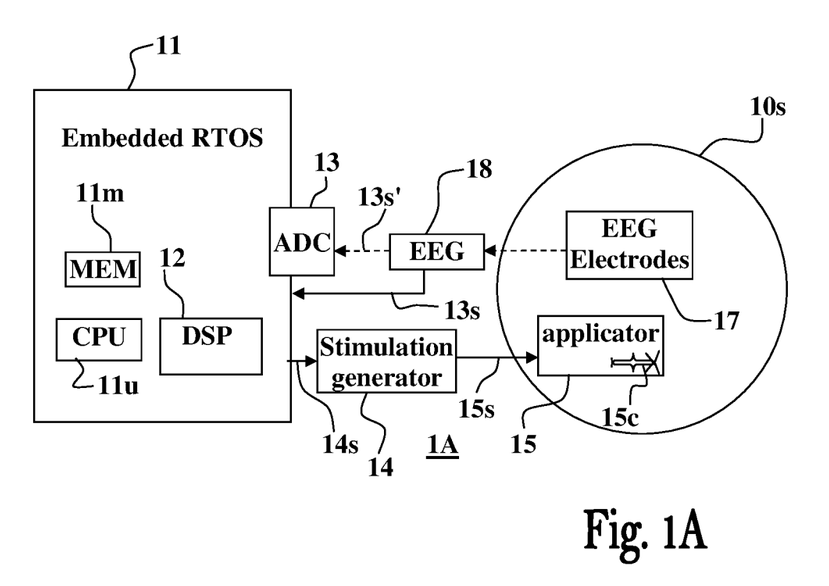
FIG. 1A to 1C are block diagrams schematically illustrating a brain stimulation system according to some possible embodiments.

FIG. 1A is a block diagram of a brain stimulation system 1A, configured in some possible embodiments for closed loop triggering and adjusting of non-invasive brain stimulation based on real time brain state indications. The system 10 comprises a real-time brain state monitoring and stimulating system 11 configured and operable to continuously, periodically or intermittently, read from an electroencephalogram (EEG) unit 18 EEG data/signals 13s/13s' (also referred to herein as brain state data/signals) indicative of brain waves measured by EEG electrodes 17 positioned on the head 10s of a subject, process the received EEG data/signals 13s/13s', and generate corresponding brain stimulation parameters and/or timing data 14s (generally referred to herein as stimulation data) for use by a stimulation generator 14. The stimulation generator 14 is configured and operable to generate stimulation signals 15s used by a stimulation applicator 15 to apply stimulation to at least one area/region of the brain of the treated subject. The real-time brain state monitoring and stimulating system 11 comprises one or more processors 11u, memories 11m, configured and operable to use a real-time operating system (RTOS) for operating a digital signal processing (DSP) unit 12 internally embedded into the brain state monitoring and stimulating system 11.

Figure 1B:
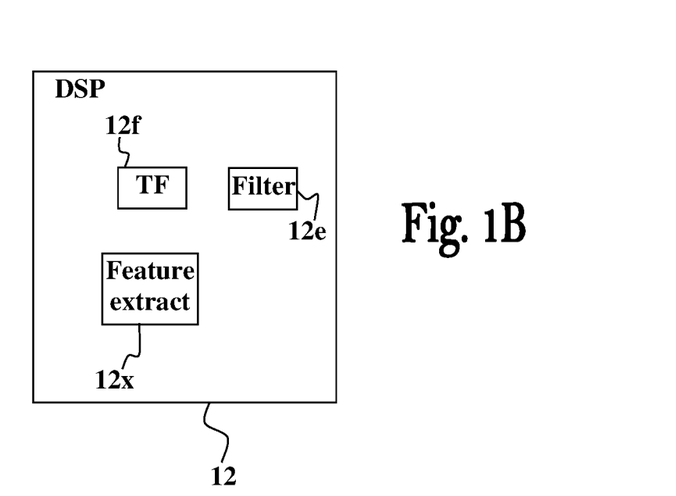

The DSP unit 12 is configured and operable to process the brain state data/signals 13s/13s' and based thereon generate brain stimulation parameters and/or timing data 14s supplied to the stimulation applicator. FIG. 1B shows components of the DSP unit 12 according to some possible embodiments, comprising a filter unit 12e configured to remove interferences/artifacts from the brain state data/signals 13s/13s', an analysis unit 12f configured to process and analyze the brain state data/signals 13s/13s', and a feature extraction unit 12x configured to determine one or more brain state features based on the brain state data/signals 13s/13s'. The DSP unit can be configured to generate the brain stimulation parameters and/or timing data 14s based on the one or more brain state features from the feature extraction unit 12x.

In some embodiments, the real-time brain state monitoring and stimulating system 11 and all its components are implemented in a single integrated circuit device.

Figure 1C:
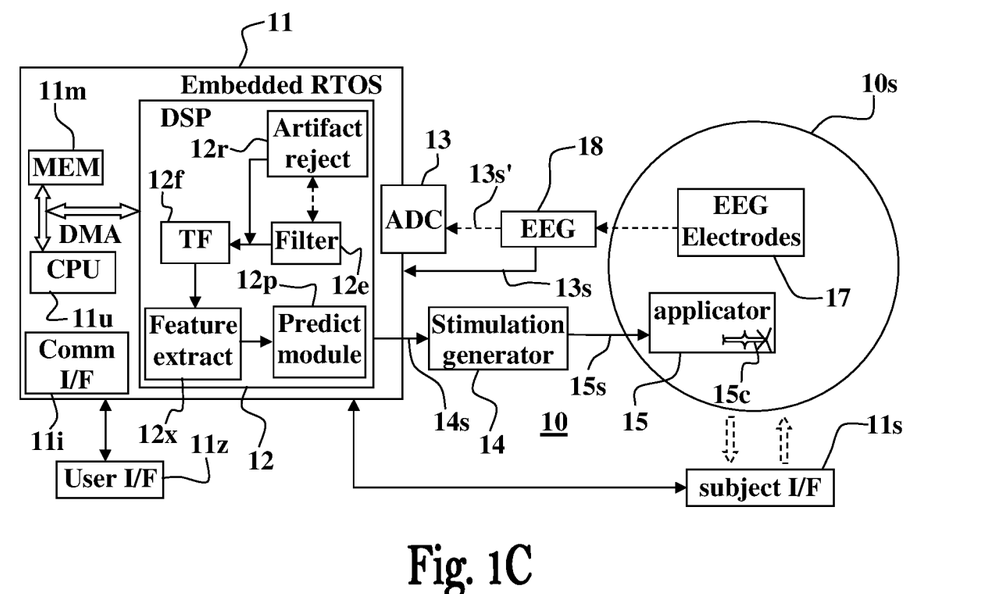

FIG. 1C is a block diagram of a brain stimulation system 10, configured in some possible embodiments for closed loop triggering and adjusting of non-invasive brain stimulation based on real time brain state indications. The system 10 comprises a real-time brain state monitoring and stimulating system 11 configured and operable to continuously, periodically or intermittently, read from an electroencephalogram (EEG) unit 18 EEG data/signals 13s/13s' indicative of brain waves measured by EEG electrodes 17 positioned on the head 10s of a subject, process the received EEG data/signals 13s/13s', and generate corresponding brain stimulation parameters and/or timing data 14s (generally referred to herein as stimulation data) for use by a stimulation generator 14. The stimulation generator 14 is configured and operable to generate stimulation signals 15s used by a stimulation applicator 15 to apply stimulation to at least one area/region of the brain of the treated subject (10s e.g., by TMS coils, and/or sound/voice generator/player, and/or current stimulating electrodes, and/or 2D/3D display/holographic device, and/or haptic/tactile stimulator transducers).

The real-time brain state monitoring and stimulating system 11 is configured in some embodiments to determine the brain state of the treated subject (10s) by analyzing EEG rhythms reflected from the received EEG data/signals 13s/13s', predict based on the determined EEG rhythms at least one brain state about to occur in the brain of the treated subject (10s), and based on the determined and/or predicted brain state(s) generate one or more the brain stimulation parameters and/or timing data 14s (e.g., frequency, and/or amplitude, and/or timing) to be used by the stimulation generator 14 for generating stimulation signals 15s for stimulating the brain of the treated subject (10s) by the stimulation applicator 15.

The brain state signals 13s' from the EEG unit 18 are digitized by an analog-to-digital converter (ADC) 13, which can be an integral unit embedded in the real-time brain state monitoring and stimulating system 11, or a unit external to the real-time brain state monitoring and stimulating system 11. In this specific and non-limiting example, the brain stimulation generator 14 is configured to generate stimulation signals 15s for use by one or more electromagnetic coils 15c of the applicator 15, such as TMS coils, configured to induce magnetic fields in brain tissue of the treated subject (10s). However, other brain stimulation techniques can be similarly used by the brain stimulation generator 14 and applicator 15 units, such as described hereinabove and herein below, when operated in closed-loop orchestrated by the real-time brain state monitoring and stimulating system 11.

The real-time brain state monitoring and stimulating system 11 comprises one or more processors 11u and memories (e.g., RAM, SDRAM, FLASH) 11m, configured and operable to use a real-time operating system (RTOS) for operating a digital signal processing (DSP) unit 12 internally embedded into the brain state monitoring and stimulating system 11. The DSP unit 12 is configured and operable to carry out data filtration, spectral analysis functions, feature extractions, brain state prediction, and determine operational parameters and/or timing data to be used by the brain stimulation generator 14 in the generation of the stimulation signals 15s.

Since processing speed is essential for the accurate determination of the brain state of the treated subject (10s) in real time, the one or more processing units 11u of the real-time brain state monitoring and stimulating system 11 operated by the RTOS, and the memory 11m, are implemented in a single hardware device, and the DSP unit 12 is implemented as a separate hardware unit e.g., FPGA/GPU implementation. In order to optimize the system performance, the one or more processors 11u and/or DSP unit 12, are configured to utilize a high speed data communication protocol (e.g., FCP), and/or with direct memory access (DMA), to thereby prevent the inevitable 'handshaking' delays typical required in conventional systems, wherein the processing units are required to handle the memory access operations.

For example, when implemented utilizing DMA, the one or more processors 11u and the DSP unit 12 can independently perform data read and write operations from/in the memory 11m, without one unit interrupting the continuous data processing operation of the other. Accordingly, the use of DMA and/or high speed communication protocol(s) in the brain state monitoring and stimulating system 11 releases the load off the one or more processors 11u, generally responsible for acquiring the brain state data/signals 13s/13s'. This configuration of the brain state monitoring and stimulating system 11 enables the one or more processors 11u to be more efficient and relay the data in real time with low delay times. The DSP unit 12 is further configured to determine operational parameters and scheduling/timing data 14s, and output the same to the brain stimulation generator 14.

Table 1 demonstrates improvements in data processing speed that can be achieved by the above described hardware implementation of the brain state monitoring and stimulating system 11 according to some possible embodiments. This design significantly speeds-up the data collection and processing operations, which thus allows collection of greater amounts of data within shorter time periods, with which the prediction algorithms can provide more accurate and longer term predictions of the brains waves, and which enables precise triggering and modulation of the of brain stimulation pulses.

Zrenner et al., (2018) required that the measured power of alpha brainwave band be at least 25% of the total measured power i.e., of all brain waves bands, in order to perform the phase locking. This power limitation can be overcome with the brain stimulation system 10 due to its improved processing speed, which allows for better prediction accuracy even for weaker or noisier signals.

The DSP unit 12 comprises in some embodiments a digital filter module 12e configured and operable to remove interfering signals from the EEG signals/data 13s'/13s digitized by the ADC 13 e.g., using infinite impulse response (IIR, e.g., Butterworth or Elliptical filter) filter, finite impulse response (FIR). The DSP unit 12 comprises a time-frequency (TF) analysis module 12f configured and operable to carry out spectral analysis (e.g., utilizing fast Fourier transform—FFT) and time-frequency analysis to the filtered EEG signals/data from the filter module 12e, and generate data indicative thereof, a feature extraction module 12x configured and operable to analyze the processed and filtered measured data generated by the analysis module 12f and determine based thereon one or more brain state features (e.g., dominant frequency bands in the filtered measured data, phase data, amplitude data, and suchlike), and generate feature data indicative thereof. The brain state prediction module 12p is configured and operable to process the features data generated by the feature extraction module 12x, predict at least one brain state that is about to occur in the brain of the treated subject (10s), and generate based on the predicted at least one brain state operational parameters and/or timing data 14s used for generating one or more brain stimulations by the stimulation generator 14.

Optionally, and in some embodiments preferably, the DSP unit 12 comprises an artifacts rejection module 12r configured and operable to process the EEG signals/data 13s'/13s received from the EEG unit 18. The artifacts rejection module 12r is particularly advantageous in embodiments utilizing electromagnetic coils 15c (e.g., TMS coils) in the applicator 15, because the magnetic fields generated by the coils 15c impose strong artifacts on the EEG data/signal 13s/13s' measured by the EEG unit 18, and thus complicates the analysis of the EEG data/signal 13s/13s'. It is however noted that artifacts can be introduced into the EEG data/signal 13s/13s' from multiple different sources, such as for example, electrical sources, eye blinks, movements, muscle contraction, heart pulses, electrode movement, mechanical pressure on the electrode, and suchlike.

TABLE 1

FFT results
FFT Benchmark 262,155 Points

| Benchmark | CPU | | | | | GPU | |
| --- | --- | --- | --- | --- | --- | --- | --- |
| | 2 Threads | 4 Threads | 8 Threads | 12 Threads | 24 Threads | Max Threads | FPGA Virtex-5 |
| FFT | 76.17 ms | 45.41 ms | 31.63 ms | 27.85 ms | 31.36 ms | 8.13 us (Execution) | 2.59 ms |

(from C. Cullinan, et al., MathWorks 2012)

The improvements in the processing speed, and the prediction accuracy, obtained by the brain stimulation system 10 also allow for expanding the utility of the system to subjects for which the power of the measured alpha, or other, brainwave band is relatively low, and thus were not suitable for treatment by prior art implementations. For example, the algorithms used for the phase locking in the system of In some embodiments the analysis module 12f is configured and operable to analyze the EEG data/signal 13s/13s' measured by the EEG unit 18 within time windows of up to 100 ms after the application of brain stimulations by the applicator 15 e.g., TMS pulse applied by coils 15c, which can be substantially difficult to carry out due to the induced artifacts. Typically, such artifacts are removed in conventional brain stimulation systems by a manual post processing analysis stage which aims to eliminate the described artifacts by rejecting specific components extracted using independent component analysis (ICA). Although ICA is considered robust and provides good results, it is a time consuming process/algorithm not suitable for the real-time brain stimulation systems disclosed herein. The artifacts rejection module 12$r$ is thus implemented in some embodiments (by hardware, software, or a combination of hardware and software) utilizing a real-time ICA process configured to remove the artifacts from the EEG data/signal 13$s$/13$s'$ in real time e.g., within time windows of about 100 to 600 ms, optionally about 150 to 500 ms, and in some embodiments about 200 ms, from acquisition of the brain state data/signals 13$s$/13$s'$.

The artifacts rejection module 12$r$ can be configured and operable to remove artifacts from the EEG signals/data 13$s'$/13$s$ and pass substantially artifacts-free EEG signals/data to the filter unit 12$e$ for signal filtration. Alternatively, in some possible embodiments the artifacts rejection module 12$r$ is configured and operable to receive the filtered EEG signals/data generated by the filter module 12$e$, process the received filtered EEG signals/data to remove the artifacts therefrom, and pass the substantially artifacts-free and filtered EEG signals/data to the analysis module 12$f$.

In some embodiments the different components of real-time brain state monitoring and stimulating system 11 operated by the RTOS is implemented in a single chip device (e.g., on a single semiconductor substrate as a SoC). For example, in a SoC implementation of the real-time brain state monitoring and stimulating system 11 the one or more processing units 11$u$ can be implemented in a FPGA, and the DSP unit 12 by a GPU of the SoC. This way, the DMA, and all electrical connections, are internally formed/patterned inside the chip, without the discrete components and printed circuit boards typically required. Such SoC implementations improves data communication speeds, and substantially reduces geometrical dimensions of the system, because all the components of the system 11 are implemented and interconnected on the same semiconductor substrate of the chip.

Non-invasive brain stimulation has been shown to be of therapeutic benefit for a range of neurological and psychiatric indications each with its own protocol and thus each could be optimized by application during different brain states. Thus, in some embodiments, the operational parameters data 14$s$ determined by the prediction module 12$p$ for adjusting the stimulation signals 15$s$ generated by the stimulation generator 14 can comprise one or more of the following: stimulation signal amplitude, and/or stimulation signal frequency and/or timing, and/or brain region/area of the treated subject to be stimulated.

In some embodiments the system 10 comprises a user interface unit 11$z$ configured to present information to the user/practitioner and receive from the user/practitioner various data inputs. For example, and without being limiting, the user interface unit 11$z$ can be configured allow the user/practitioner to specify at least one of the following parameters/options:

(1) input sources/electrode(s) (e.g., EEG electrodes 17, and/or specific tACS electrodes 17', and/or fMRI signals/data, and/or cognitive task response from the subject interface unit 11$s$) to be used by the analysis module 12$f$ and feature extraction module 12$x$ to determine the brain state of the subject, including option for targeting electrodes over multiple brain regions/areas for measures of brain connectivity;

(2) preprocessing steps to be performed by the DSP unit 12, such as but not limited to referencing, filtering and source localization;

(3) Target frequency band and phase to be used by the stimulation generator 14;

(4) power threshold of target frequency band to be used by the stimulation generator 14;

(5) Time window for analysis by the analysis module 12$f$ and for the feature extraction module 12$x$;

(6) analysis type to be performed by the analysis module 12$f$ and the feature extraction module 12$x$;

(7) predictive model to be used by the prediction module 12$p$;

(8) output stimulation pattern(s) to be applied by the stimulation generator 14.

The prediction module 12$p$ can be thus configured and operable to determine the operational parameters/stimulation data 14$s$ to be used for adjusting the stimulation signals 15$s$ generated by the generator 14 based on the features extracted from the input data/signals and/or the above-mentioned parameters/options (1) to (8) as set by the operator/practitioner via the user interface unit 11$z$. User/practitioner specification is essential in some embodiments as different applications call for not only identifying specific brain states but also require a different balance of speed and precision. Instantaneous phase locking by definition requires high speed as the phase changes continuously. The brain stimulation system embodiments hereof configured to operate at such high speeds for analysis of instantaneous phase with the required high temporal precision. It is however noted that the brain stimulation system can also utilize analysis types requiring less temporal precision, such as event related desynchronization (ERD), which provides higher stability of the analysis, and which also opens the ability to add other aspects to the analysis pipeline. For example, this may be reflected in the choice of source localization process used by the feature extraction module 12$x$, which may utilize in case ERD is used a more precise but slower process e.g., utilizing Laplacian transform, or a still accurate but faster process e.g., utilizing Hjorth transform.

Another non-limiting example is the choice of predictive model employed by the prediction module 12$p$. In some possible embodiments the stimulation system 10 is configured to use a suite of options, such as but not limited to, autoregressive forward prediction model, modeling based on the peak frequency in the FFT transform, and back propagating feedback model, to update the prediction module 12$p$ over time. The prediction module 12$p$ can be configured to determine correlation of the brain state data/signals 13$s$/13$s'$ from the EEG unit 18 with brain state patterns previously measured by the system in the current, or previous, sessions, and based on the correlation predict future brain states likely to occur in the brain of the treated subject, and accordingly determine the stimulation data 14$s$ supplied to the stimulation generator 14.

The stimulation data 14$s$ provided by the brain state monitoring and stimulating system 11 to the brain stimulation generator 14 comprises in some embodiments instructions for triggering a predetermined stimulation pattern that is aligned to the targeted brain state, and/or instructions to apply different patterns specified for different brain states. Accordingly, the stimulation generator 14 can be configured to be compatible with transcranial magnetic stimulation (TMS) procedures, transcranial direct current stimulation (tDCS) procedures, and/or transcranial electrical stimulation (TES) procedures.

In some embodiments the brain stimulation system comprises a subject interface unit 11s configured and operable to interact with the treated subject for inducing desired brain states in the treated subject. The subject interface unit 11s can be configured to play to the treated subject audio-visual content configured to induce the desired brain state, and/or present to the treated subject specially designed (e.g., cognitive) tasks, and optionally receive corresponding inputs/feedbacks therefrom, usable by the system 10 for inducing dependent brain state e.g., achieved by input of external triggers.

Figure 2:
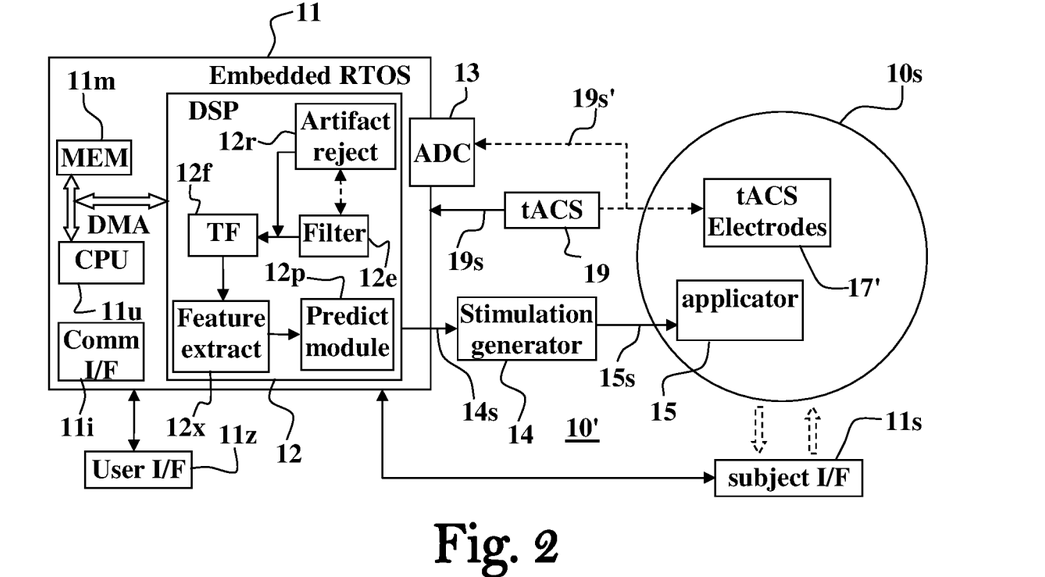
FIG. 2 is a block diagram schematically illustrating a brain stimulation system according to some possible embodiments utilizing transcranial alternating current stimulation for determining brain states of a treated subject.

FIG. 2 is a block diagram of a possible embodiment of a brain stimulation system 10', that is substantially similar to the brain stimulation system 10 shown in FIG. 1, but which utilizes tACS data 19s to determine brain states of the treated subjects, instead of the EEG data/signals. In this example the brain stimulation system 10' further comprises a tACS unit 19 configured and operable to induce desired brain states in the brain of the treated subject by the tACS electrodes 17' (e.g., entrain the subject's brain rhythms to a given frequency and phase). Optionally, the brain stimulation system 10' can be configured to receive the tACS signals 19s' applied to the treated subject by the tACS electrodes 17', and digitize the received tACS signals 19s' by the ADC 13. The tACS data/signals 19s/19s' can be similarly processed by the brain state monitoring and stimulating system 11, as described hereinabove, to remove artifacts and/or filter interferences by the artifacts rejection module 12r and the filter module 12e, analyze the filtered and/or artifacts-free tACS data/signals by the analysis module 12f, to predict at least one brain state about to occur in the brain of the treated subject and generate corresponding stimulation parameters and/or timing data 14s by the brain state prediction module 12p for adjusting/regulating the stimulation signals 15s generated by the stimulation generator 14. The subject interface unit 11s can be similarly used for inputting external triggers, such as but not limited to behavioral performance, thereby making the triggering by the brain state task dependent.

Figure 3:
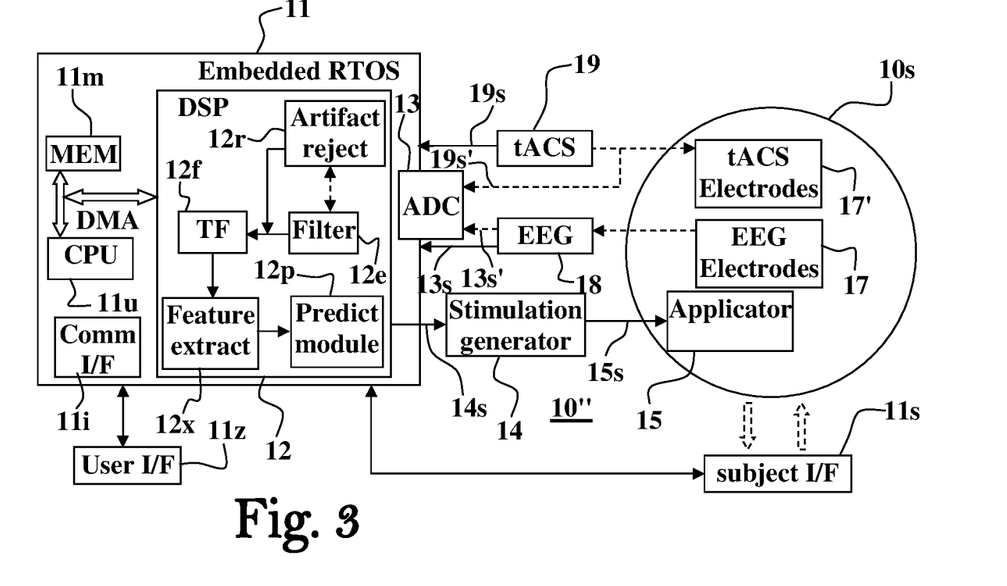
FIG. 3 is a block diagram schematically illustrating a brain stimulation system according to some possible embodiments utilizing EEG signals and transcranial alternating current stimulation signals/data for determining brain states of a treated subject.

FIG. 3 is a block diagram schematically illustrating a brain stimulation system 10" utilizing the EEG signals/data 13s'/13s and the tACS signals/data, 19s and/or 19s', for determining brain states of the treated subject (10s). The brain stimulation system 10" can be configured to select only the EEG data/signals 13s/13s', only the tACS signals/data, 19s and/or 19s', or both EEG and tACS signals/data, to predict at least one brain state about to occur in the brain of the treated subject, and use the same to generate corresponding stimulation parameters and/or timing data 14s for adjusting/regulating the stimulation signals 15s applied by the stimulation generator 14, as described hereinabove.

Figure 4:
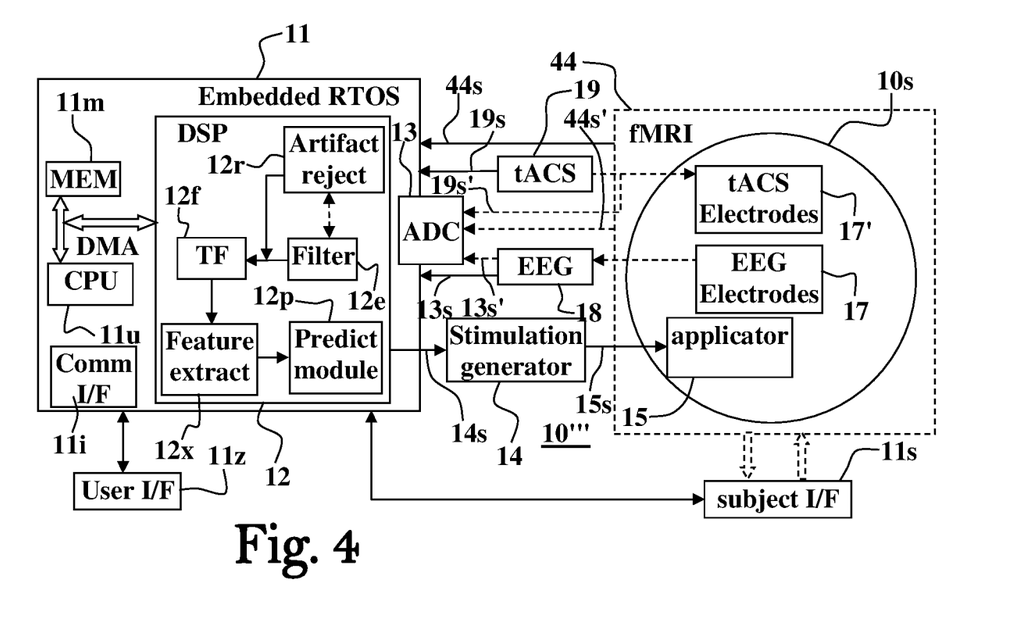
FIG. 4 is a block diagram schematically illustrating a brain stimulation system according to some possible embodiments utilizing fMRI data/signals for determining brain states of a treated subject.

FIG. 4 is a block diagram schematically illustrating a brain stimulation system 10''' configured to use fMRI data 44s and/or signals 44s', from fMRI system 44, for determining brain states of a treated subject. The fMRI system 44 is configured to measure brain activity of the subject (10s), and the brain stimulation system 10''' is configured and operable to predict at least one brain state about to occur in the brain of the treated subject based on the signals/data from the fMRI system 44, and use the same to generate corresponding stimulation parameters and/or timing data 14s for adjusting/regulating the stimulation signals 15s applied by the stimulation generator 14, as described hereinabove.

As demonstrated in FIG. 4, the brain stimulation system 10''' can be configured and operable to combine signals/data 13s'/13s received from the EEG electrodes 17, and/or the tACS signals/data 19s'/19s, with the fMRI data/signals 44s/44s, and use the signals/data received from the various sources to extract the brain state features for the prediction and/or the generation of the stimulation data 14s.

As shown if FIGS. 1 to 4, the real-time brain state monitoring and stimulating system 11 can comprise a communication interface module 11i configured and operable to handle the data communication with the EEG unit 18, and/or the tACS unit 19, and/or the fMRI system 44, and/or user interface unit 11z, and/or the subject interface unit 11s, and/or the stimulation generator 14. The communication interface module 11i can be configured to communicate data with the various units/systems over electrically conducting wires using, for example, serial (e.g., USB, UART, or suchlike) or parallel (ISA, ATA, SCSI, PCI, or suchlike) bus data communication protocols, and/or wireless data communication (e.g., WiFi, Bluetooth, Zigbee, or suchlike). Accordingly, in embodiments wherein the components of the real-time brain state monitoring and stimulating system 11 are embedded in a single integrated circuit (IC) device, the communication interface module 11i is also embedded into the IC of the system 11.

Figure 5:
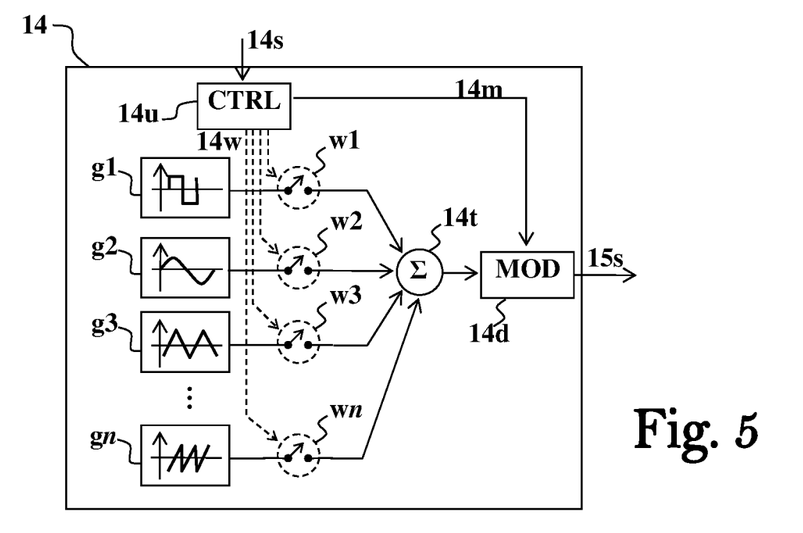
FIG. 5 is a block diagram of an applicator unit configured to adapt in real-time the shape and/or timing of stimulation signal applied by the system according to some possible embodiments.

FIG. 5 is a block diagram of a possible stimulation generator 14 configured to adjust in real time signals applied by the system to the brain of the treated subject based on the brain stimulation parameters and/or timing data 14s generated by the brain state monitoring and stimulating system 11. In this specific and non-limiting example, the stimulation generator 14 comprises a control unit 14u configured and operable to receive the brain stimulation parameters and/or timing data 14s and generate based thereon control signals 14w and/or 14m for adjusting in real-time the shape and/or scheduling and/or patterns of the stimulation signals 15s supplied to the stimulation applicator 15.

The stimulation generator 14 may comprise a plurality of signal sources g1, g2, g3, . . . , gn, each associated with a respective switch unit w1, w2, w3, . . . , wn, and configured to generate a specific waveform having a desired shape and frequency. The frequency of the waveform generated by each signal source g1, g2, g3, . . . , and gn, can be determined by controlled signals (not shown) generated by the control unit 14u based on the brain stimulation parameters and/or timing data 14s. The control unit 14u is configured and operable to select the waveforms of the stimulation signal 15s by generating respective control signals 14w signals for changing the states of the respective switch unit w1, w2, w3, . . . , wn, to thereby select the waveforms supplied to a signal summation unit 14t.

The signal summation produced by the summation unit 14t can be inputted to a signal modulation unit 14d configured and operable to modulate it with signal patterns provided through the signals/data 14m from the control unit 14u. It is noted that modulation of the signal from the summation unit 14t is not essentially required in all brain stimulation sessions, so the signals/data 14m from the control unit 14u can be accordingly used to instruct the modulator 14d to pass the signal from the summation unit 14t as is, without applying any modulation.

Figure 6:
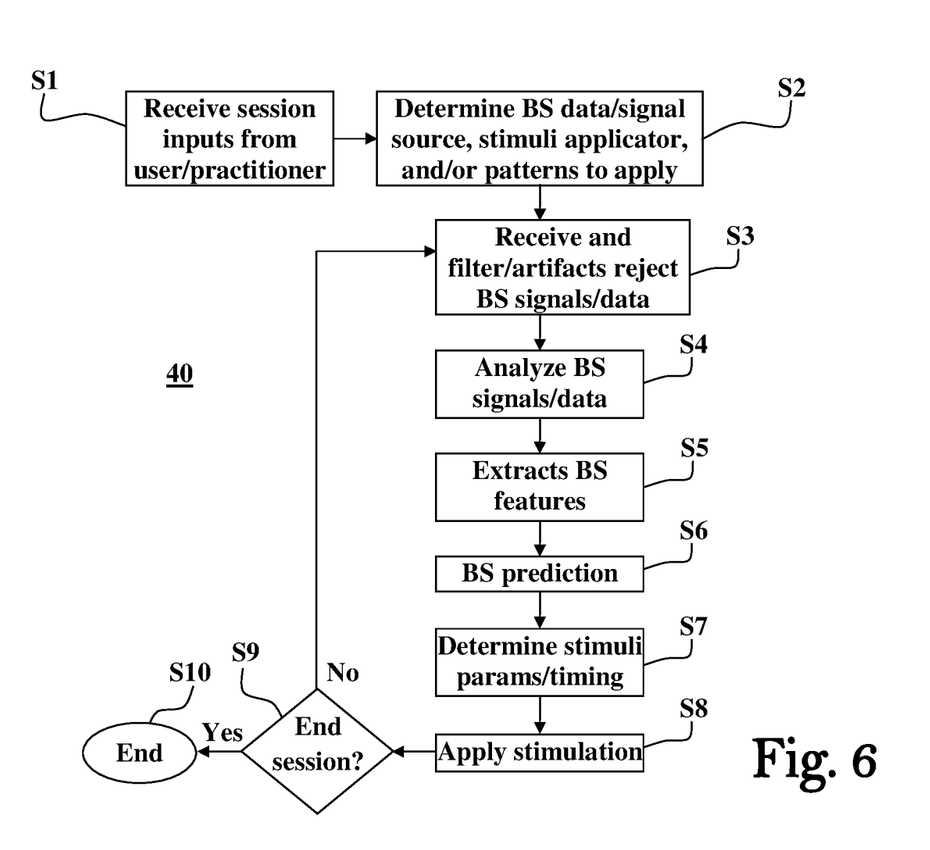
FIG. 6 is a flowchart exemplifying a closed-loop brain stimulation process according to some possible embodiments.

FIG. 6 is a flow chart exemplifying a closed-loop brain stimulation process 40 according to some possible embodiments. The brain stimulation process 40 starts in step S1 wherein the brain stimulation system receives session inputs form the user/practitioner via the user interface unit 11z (e.g., parameters/options (1) to (8) described hereinabove). In step S2 the system determines based on the inputs received in step S1 the brain state (BS) data/signal source to be used in the session (e.g., EEG signals, tACS signals, and/or fMRI data), which devices are to be used to apply the brain stimulations (e.g., coils and/or electrode selection for targeting desired brain region/area, and/or sensory applicators), and/or the signal patterns that should be applied to the treated subject.

In step S3 the system receives and filters, and/or remove artifacts from, the brain state signals/data. The filtered and/or artifacts-free signals/data is then analyzed in step S4 (e.g., spectral analysis and/or time-frequency analysis), and in step S5 the system extracts one or more brain state features from the analyzed processed and filtered and/or artifacts-free brain state signals/data. Next, in step S6 one or more brain states about to occur in the brain of the treated subject are predicted by the system, and in step S7 the system determines operational parameters and/or timing data to be used by the stimulation applicator for applying in step S8 the stimulation signals.

In step S9 it is checked whether the brain stimulation session is to be ended. If further brain stimulation is to be applied then steps S3 to S8 are repeated any number of times required until it is determined in step S9 that the session should be ended by stopping the stimulations applied by the applicator and moving the control to step S10. It is noted that the application of brain stimulating signals of step S8 can be continuously continued as the steps S3 to S8 are repeated, and that the applied brain stimulating signals can dynamically change during these steps as new stimulation parameters and/or timing data is generated in step S7, to adjust the applied brain stimulations to the changes occurring in the brain state of the treated user.

It should also be understood that in the process 40, or method(s) shown or described herein, the steps of the process/method may be performed in any order or simultaneously, unless it is clear from the context that one step depends on another being performed first. The process 40, or one or more of its steps, may be realized as computer executable code created using a structured programming language (e.g., C), an object oriented programming language such as C++, or any other high-level or low-level programming language (including assembly languages, hardware description languages, and database programming languages and technologies) that may be stored, compiled or interpreted to run on a computer device, as well as heterogeneous combinations of processors, processor architectures, or combinations of different hardware and software.

The data processing of the brain stimulation system disclosed herein may be distributed across a number of computerized, devices, which may be functionally integrated into a dedicated standalone stimulation system. All such permutations and combinations are intended to fall within the scope of the present disclosure.

Figure 7:
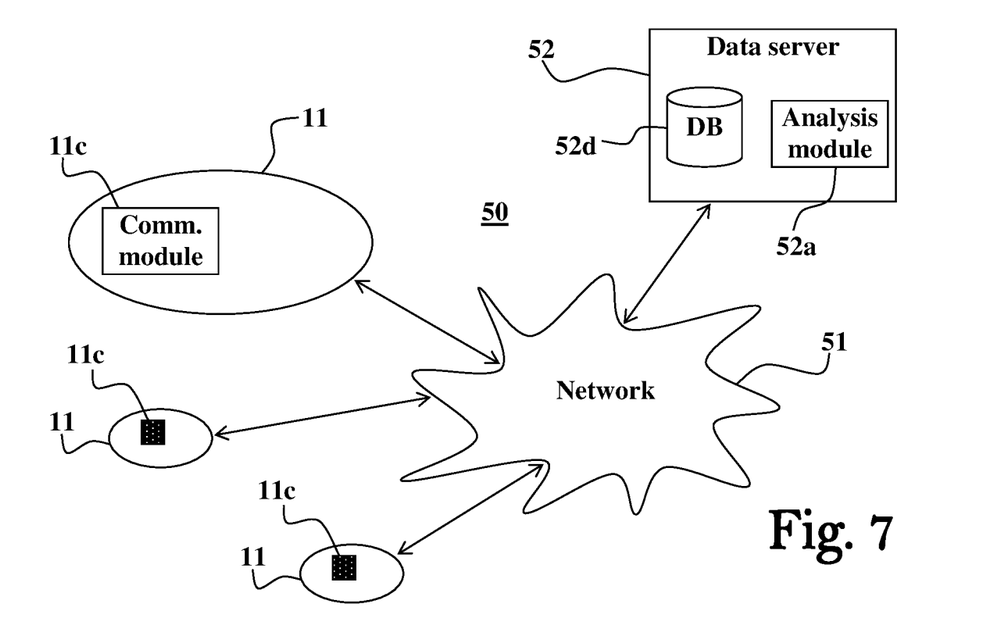
FIG. 7 is a block diagram of a data processing and analysis system according to some possible embodiments.

FIG. 7 shows a data processing and analysis system 50 according to some possible embodiments. The system 50 comprises a plurality of real-time brain state monitoring and stimulating systems 11, each having a communication module lie configured and operable to communicate data over a data network 51 e.g., the Internet. In some embodiments a data server 52 is used to receive and log treatment data associated with the treatment protocols conducted by the plurality of real-time brain state monitoring and stimulating systems 11, and treatment progress and results obtained using the treatment protocols. The data received from the plurality of real-time brain state monitoring and stimulating systems 11 can be stored in a database 52d maintained by the data server 52. The data server 52 can be implemented by a computer system having one or more processors (not shown), memories (e.g., volatile and non-volatile—not shown), and data communication modules (not shown), as typically used in data servers.

In some embodiments an analysis module 52a is used in the data server 52 to process the protocol and treatment results data stored in the database 52d, and identify from the data accumulated over time treatment protocols that presented satisfactory results. The analysis module 52a can be thus configured to utilize statistical analysis and/or machine learning tools for identifying treatment protocols for which high percentage of treatment sessions show beneficial therapeutic effects. Optionally, and in some embodiments preferably, the analysis module 52a is configured to utilize artificial intelligence tools for analyzing the data accumulated in the database 52d, such as but not limited to, neural-network, machine/deep learning algorithm, and suchlike. Accordingly, the analysis of the treatment data accumulated in the database 52d can be used to generate state and predictive biomarkers and/or statistics of protocols and/or their outcomes.

The data server 52 can be configured to transfer to the plurality of real-time brain state monitoring and stimulating systems 11 analysis data indicative of the treatment protocols having the highest scores of the treatments of certain neurological/psychiatric conditions. The real-time brain state monitoring and stimulating systems 11 can be configured to generate and transmit to the data server 52 queries to scan the database 52d and look for treatment protocols that been reported to provide satisfactory results in treating a certain neurological/psychiatric condition. The real-time brain state monitoring and stimulating system 11 can be accordingly configured to receive response data from the data server 52 with statistical analysis of the analysis module 52a concerning the issued query, and present to the user/practitioner the response data in the user interface unit 11z.

Figure 8:
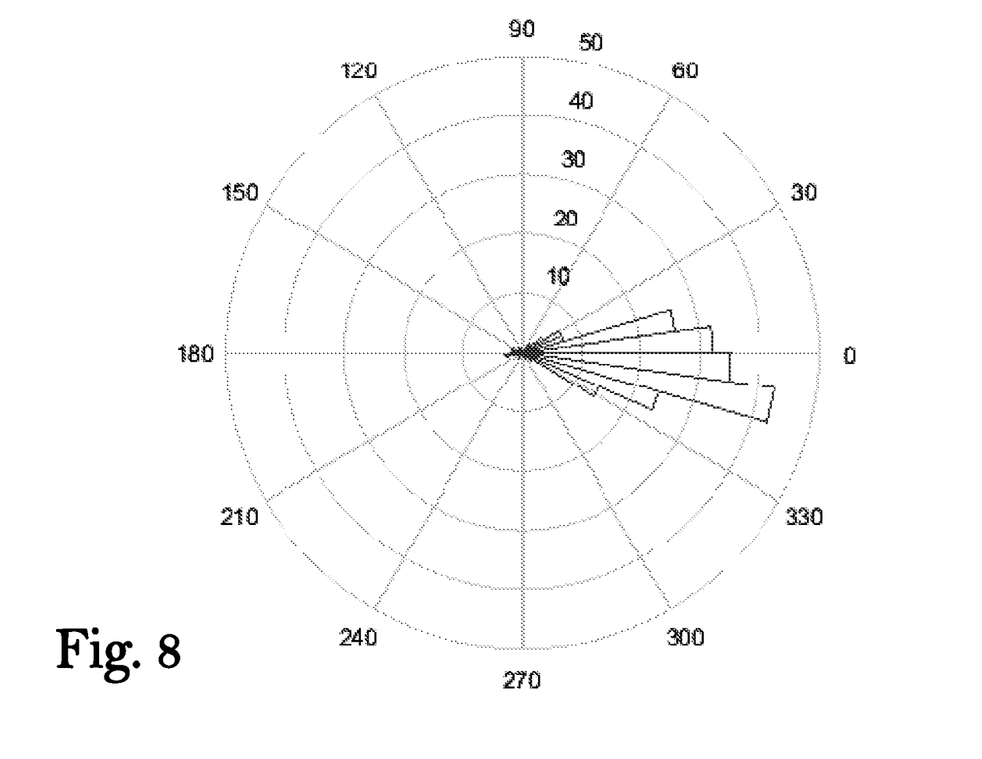
FIG. 8 shows an angle histogram of experimental results obtained using a brain stimulation system according to an embodiment of the present application.

FIG. 8 shows an angle histogram (roseplot) of application of experimental stimulation carried using implementation of the brain stimulation system shown in FIG. 1. This plot shows the actual phase angle distribution at the time of the trigger when set to 0° (zero degrees) for a representational raw EEG trace. The standard deviation here is about 38°, despite the fact that the percentage of the alpha band of the total measured power is less than 1%. This is thus an improvement over the prior art of Zrenner et al., 2018 who's algorithm is restricted to subjects who's percentage of the alpha band from the total measured power is required to be over 25% of the total power, and which resulted in a standard deviation of 53°. As such, the brain stimulation process disclosed herein, and its implementations, are clearly more precise, and more effective to a larger population of subjects.

Functions of the brain stimulation systems described hereinabove may be controlled through instructions executed by a computer-based control system. A control system suitable for use with embodiments described hereinabove may include, for example, one or more processors connected to a communication bus, one or more volatile memories (e.g., random access memory—RAM) or non-volatile memories (e.g., Flash memory). A secondary memory (e.g., a hard disk drive, a removable storage drive, and/or removable memory chip such as an EPROM, PROM or Flash memory) may be used for storing data, computer programs or other instructions, to be loaded into the computer system.

Those of skill in the art would appreciate that items such as the various illustrative blocks, modules, elements, components, methods, operations, steps, and algorithms described herein may be implemented as hardware or a combination of hardware and computer software.

In the embodiments disclosed herein, features of the invention are implemented primarily in hardware using, for example, hardware components such as application specific integrated circuits (ASICs), and/or field-programmable gated arrays (FPGAs), and/or system-on-chip implementations. Implementation of the hardware state machine so as to perform the functions described herein will be apparent to persons skilled in the relevant art(s). In yet another embodiment, features of the invention can be implemented using a combination of both hardware and software.

As described hereinabove and shown in the associated figures, the present invention provides a closed-loop brain stimulation system, and related methods. While particular embodiments of the invention have been described, it will be understood, however, that the invention is not limited thereto, since modifications may be made by those skilled in the art, particularly in light of the foregoing teachings. As will be appreciated by the skilled person, the invention can be carried out in a great variety of ways, employing more than one technique from those described above, all without exceeding the scope of the claims.

The invention claimed is:

1. A brain stimulation system for application of non-invasive electric, magnetic, and/or electromagnetic brain stimulation signals to a treated subject, said brain stimulation system comprising:
sensing means for acquiring brain state signals from the treated subject;
an integrated circuit device, comprising at least one processor, at least one memory, and a digital signal processing (DSP) unit operated by said at least one processor and configured to carry out the following:
process the acquired brain state signals and remove therefrom artifacts and/or interferences induced by the non-invasive electric, magnetic and/or electromagnetic brain stimulation signals applied by said brain stimulation system to the treated subject;
predict at least one brain state about to occur in the treated subject; and
generate brain stimulation data; and
a stimulation generator electrically connected to said integrated circuit device to receive the brain stimulation data from said DSP unit of said integrated circuit device, generate based on said brain stimulation data the non-invasive electric, magnetic and/or electromagnetic brain stimulation signals to be applied to the treated subject, adjust and/or regulate, in real-time at least one of shape, timing, and/or frequency of the non-invasive electric, magnetic, and/or electromagnetic brain stimulation signals applied to the treated subject.

2. The brain stimulation system of claim 1 wherein the DSP unit is configured to repeatedly receive the acquired brain state signals, predict the at least one brain state, and generate the brain stimulation data for adjusting or regulating the non-invasive electric, magnetic and/or electromagnetic brain stimulation signals based on the predicted at least one brain state, to thereby provide a closed-loop brain stimulation mechanism capable of adjusting or regulating the non-invasive electric, magnetic and/or electromagnetic brain stimulation signals by the generated brain stimulation data.

3. The brain stimulation system of claim 1 wherein the brain stimulation system is configured to modulate the non-invasive electric, magnetic and/or electromagnetic brain stimulation signals by the generated brain stimulation data.

4. The brain stimulation system of claim 1 wherein the at least one processor and the DSP unit are configured to exchange data using a fast communication protocol.

5. The brain stimulation system of claim 1 wherein the at least one processor and the DSP unit are configured to read and write data in the at least one memory by direct memory access.

6. The brain stimulation system of claim 1 wherein the DSP unit comprises at least one digital filtering module configured to remove at least some of the artifacts and/or interferences from the acquired brain state signals.

7. The brain stimulation system of claim 1 wherein the DSP unit comprises at least one artifacts rejection module configured to automatically remove at least some of the artifacts and/or interferences from the acquired brain state signals.

8. The brain stimulation system of claim 7 wherein the at least one artifacts rejection module is configured to use an automated independent component analysis process.

9. The brain stimulation system of claim 1 wherein the DSP unit comprises at least one analysis module configured to process the acquired brain state signals and perform at least one of time-frequency analysis and/or spectral analysis thereof.

10. The brain stimulation system of claim 1 wherein the DSP unit comprises at least one feature extraction unit configured to extract from the acquired brain state signals, and/or from spectral analysis data thereof, at least one feature indicative of the at least one brain state of the treated subject.

11. The brain stimulation system of claim 1 wherein the DSP unit comprises at least one prediction module configured to predict the at least one brain state about to occur the treated subject based on the acquired brain state signals, and wherein said DSP unit is configured to generate the brain stimulation data based on said predicted at least one brain state.

12. The brain stimulation system of claim 1 further comprising a communication module for communicating treatment data associated with treatment protocols conducted by the brain stimulation system.

13. The brain stimulation system of claim 12, further comprising a database system for storing the treatment data and/or other data communicated by the brain stimulation system via the communication module, said database system configured to analyze the data stored therein and generate statistical data associated therewith.

14. The brain stimulation system of claim 13 wherein the brain stimulation system is configured to utilize artificial intelligence tools in the analysis of the treatment data stored in the database system.

15. The brain stimulation system of claim 1 wherein the sensing means comprises at least one of EEG electrodes, tACS electrodes, or fMRI equipment.

16. The brain stimulation system of claim 1 wherein the brain stimulation system is configured to apply audio and/or visual stimulation to the treated subject, and/or require the treated subject to perform cognitive tasks.

17. A method for generating brain stimulations utilizing the brain stimulation system of claim 1, the method comprising:
acquiring by the sensing means the brain state signals;
analyzing by the DSP unit the acquired brain state signals to determine at least one feature associated with at least one brain state of the treated subject;
predicting based on the determined at least one feature and/or the acquired brain state signals the at least one brain state about to occur the treated subject; and
generating the brain stimulation data based on the predicted at least one brain state.

18. The method of claim 17, further comprising continuously, periodically or intermittently, repeating through at least one treatment session the prediction of the at least one brain state and the generation of the brain stimulation data, for newly acquired brain state signals.

19. The method of claim 18, wherein the generated brain stimulation data is configured for adjusting and/or regulating the non-invasive electric, magnetic and/or electromagnetic brain stimulation signals in accordance with variations in the at least one feature determined from the acquired brain state signals.

20. The method of claim 19, wherein the adjusting and/or regulating comprises modulating the non-invasive electric, magnetic and/or electromagnetic brain stimulation signals in accordance with variations in the at least one feature determined from the acquired brain state signals.

21. The method of claim 17 wherein the generated brain stimulation data is associated with at least one of frequency, amplitude, stimulation pattern, current polarity, pulse shape of the non-invasive electric, magnetic and/or electromagnetic brain stimulation signals, and/or a location to which the non-invasive electric, magnetic and/or electromagnetic brain stimulation signals are being applied.

22. The method of claim 17, further comprising:
storing in a database treatment data indicative of the acquired brain state signals and/or of treatment procedures conducted by the brain stimulation system;
analyzing the treatment data accumulated in the database; and
generating analysis data indicative thereof.

23. The method of claim 22 wherein the analyzing of the treatment data comprises at least one of statistical analysis, machine learning, deep learning, or any combination thereof.

24. The method of claim 17 further comprising generating the brain stimulation data based on brain states previously induced in the brain of the treated subject responsive to the non-invasive electric, magnetic and/or electromagnetic brain stimulation signals.

25. An integrated circuit, comprising:
at least one processor;
at least one memory; and
at least one digital signal processing (DSP) unit configured to be operated by said at least one processor and instructions stored in said at least one memory of said integrated circuit to receive and process brain state signals being indicative of at least one brain state of a treated subject, remove from said brain state signals artifacts and/or interferences induced by non-invasive electric, magnetic and/or electromagnetic brain stimulation signals being applied to the treated subject, predict at least one brain state about to occur in the brain of the treated subject, and generate brain stimulation data for adjusting and/or regulating in real-time at least one of shape, timing, and/or frequency of the non-invasive electric, magnetic and/or electromagnetic brain stimulation signals to be applied to the treated subject,
wherein said at least one DSP unit comprises at least one prediction module configured to predict the at least one brain state about to occur in the brain of the treated subject based on previously acquired brain state signals.

26. The integrated circuit of claim 25, further comprising at least one digital filtering module embedded in the integrated circuit and configured to remove at least some of the artifacts and/or the interferences from the received brain state signals.

27. The integrated circuit of claim 25, wherein the integrated circuit is configured to use an automated independent component analysis process for removal of at least some of the artifacts and/or the interferences from the received brain state signals.

28. The integrated circuit of claim 25, further comprising at least one analysis module configured to process the received brain state signals and perform at least one of time-frequency analysis and spectral analysis thereof.

29. The integrated circuit of claim 25, further comprising at least one feature extraction module configured to extract at least one feature indicative of at least one brain state of the treated subject from the received brain state signals.

30. The integrated circuit of claim 25, further comprising a real-time operating system for operating the at least one processor and the at least one DSP unit.

31. The integrated circuit of claim 25, further comprising a communication interface module configured to communicate data over at least one of wireless data communication or bus conductors data communication channels.

32. The integrated circuit of claim 25 wherein at least one of the at least one processor or the at least one DSP unit is implemented in FPGA or as a GPU.

33. A brain stimulation system comprising the integrated circuit of claim 25 and a stimulation generator electrically connected to the integrated circuit and configured to receive the brain stimulation data from the at least one DSP unit and based thereon adjust and/or regulate in real-time the at least one of shape, timing, and/or frequency of the non-invasive electric, magnetic and/or electromagnetic brain stimulation signals to be applied to the treated subject.

* * * * *